United States Patent [19]
Wenstrom, Jr.

[11] Patent Number: 5,906,624
[45] Date of Patent: May 25, 1999

[54] SUTURE THREADER ASSEMBLY, SUTURE ANCHOR ASSEMBLY, AND METHOD FOR THREADING SUTURE

[75] Inventor: Richard F. Wenstrom, Jr., Norwood, Mass.

[73] Assignee: Mitek Surgical Products, Inc., Westwood, Mass.

[21] Appl. No.: 09/144,890

[22] Filed: Sep. 1, 1998

Related U.S. Application Data

[62] Division of application No. 08/778,915, Jan. 3, 1997, Pat. No. 5,800,447.

[51] Int. Cl.⁶ .................................................. A61B 17/04
[52] U.S. Cl. ............................ 606/139; 606/104; 223/99; 112/169
[58] Field of Search ..................................... 606/104, 144, 606/147, 148, 232; 223/99; 112/169

[56] References Cited

U.S. PATENT DOCUMENTS

| 2,042,403 | 5/1936 | Hrivnak | 223/99 |
| 2,167,080 | 7/1939 | Mason | 223/99 |
| 2,416,260 | 2/1947 | Karle | 223/99 |
| 4,779,616 | 10/1988 | Johnson | 606/148 |
| 5,251,797 | 10/1993 | Martin | 223/99 |
| 5,501,692 | 3/1996 | Riza | 606/148 |
| 5,827,299 | 10/1998 | Fucci et al. | 606/104 |

*Primary Examiner*—Gary Jackson
*Attorney, Agent, or Firm*—Pandiscio & Pandiscio

[57] ABSTRACT

A suture threader comprises a body having first and second ends, a first suture threader extending from the body first end, and a second suture threader extending from the body second end.

10 Claims, 8 Drawing Sheets

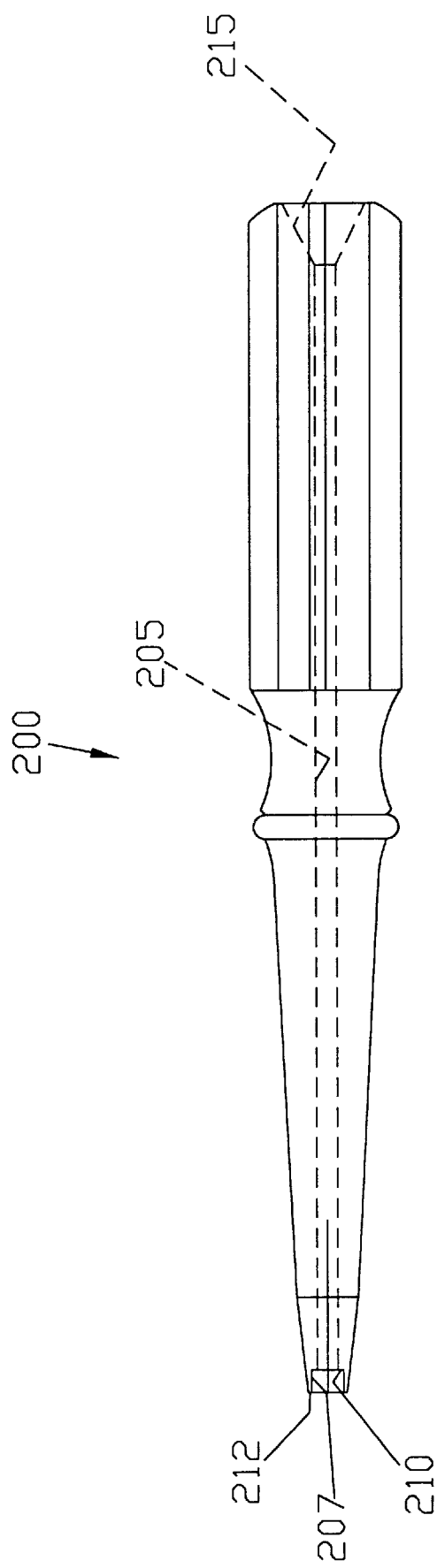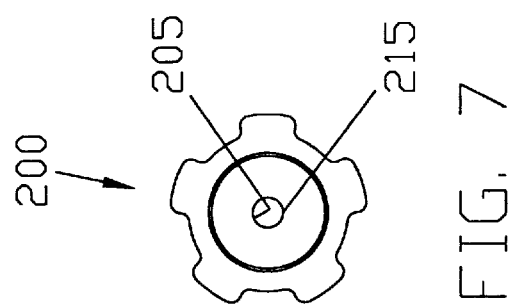

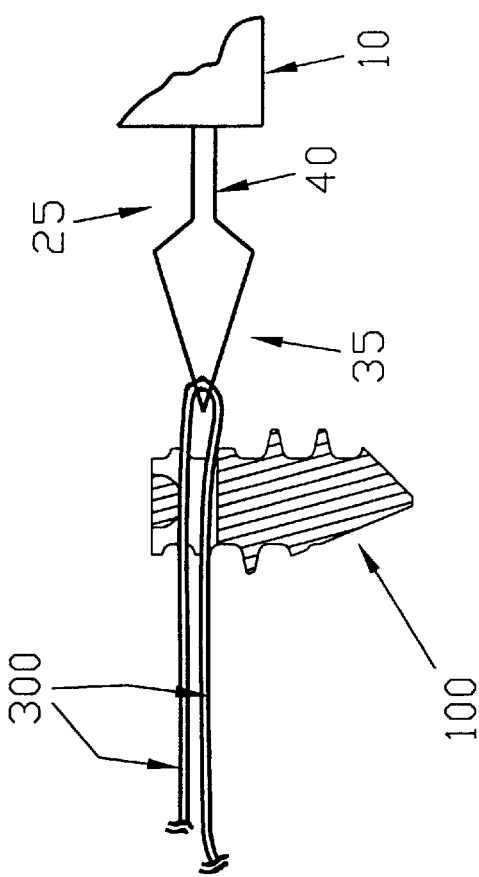
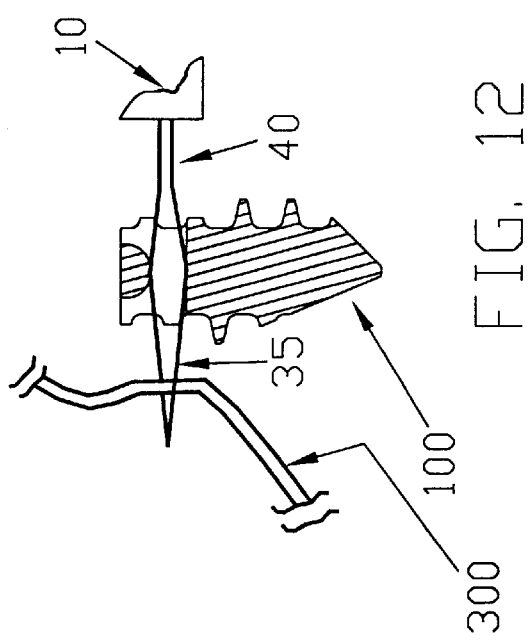
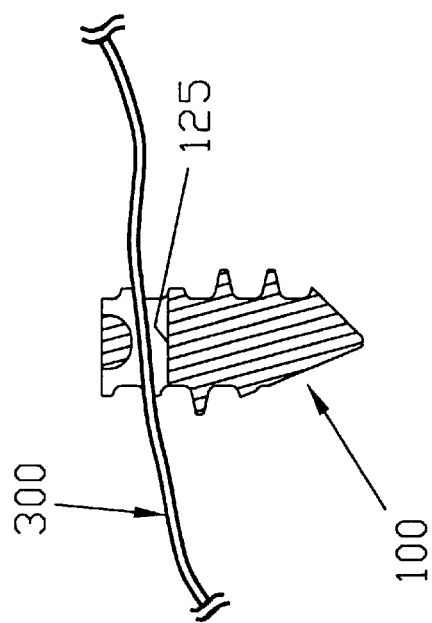
FIG. 13
FIG. 12
FIG. 14

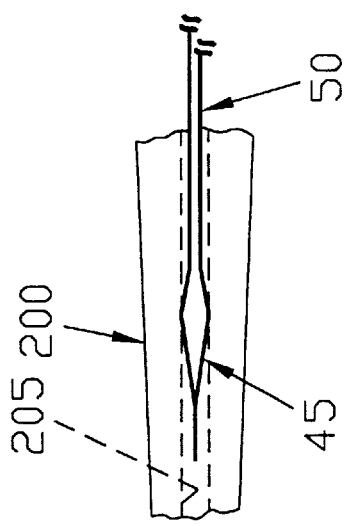
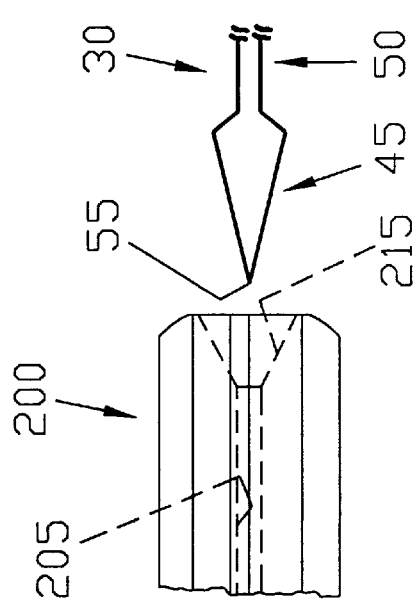
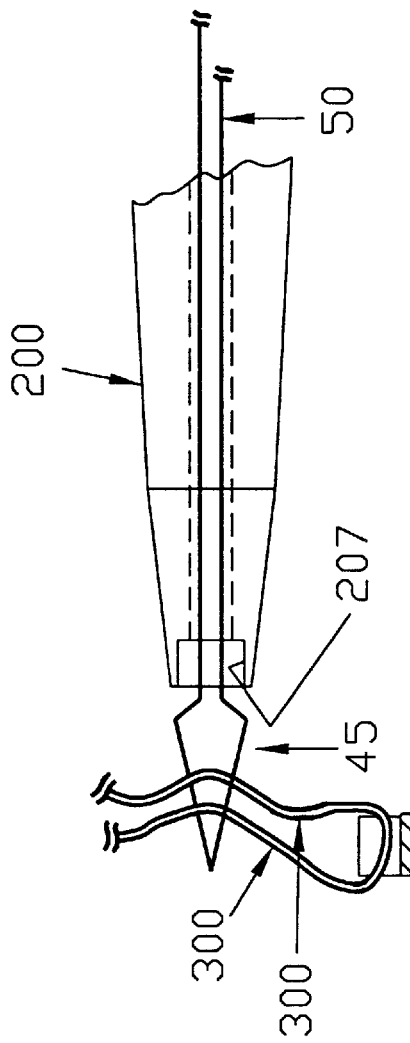

SUTURE THREADER ASSEMBLY, SUTURE ANCHOR ASSEMBLY, AND METHOD FOR THREADING SUTURE

This is a division of U.S. application Ser. No. 08/788, 915, filed Jan. 3, 1997 for "SUTURE THREADER ASSEMBLY SUTURE ANCHOR ASSEMBLY, AND METHOD FOR THREADING SUTURE", now U.S. Pat. No. 5,800, 447.

FIELD OF THE INVENTION

This invention to relates to surgical devices and procedures in general, and more particularly to suture threaders, suture anchor assemblies, and methods for threading suture.

BACKGROUND OF THE INVENTION

It is known to use a suture anchor of the sort having a transverse bore extending through a proximal portion thereof so as to facilitate attachment of the suture to the anchor. It is also known to use, in combination with the suture anchor, an inserter having a lengthwise bore extending therethrough and through which may extend the suture which is attached to the suture anchor. Such a combination is shown and described, for example, in U.S. Pat. No. 5,411,506, issued May 2, 1995 to Goble et al. for ANCHOR DRIVER, which patent is assigned to the assignee of the present patent application, and which patent is hereby incorporated herein by reference. See also U.S. patent application Ser. No. 08/514,613, filed Aug. 14, 1995 by Goble et al. for SUTURE ANCHOR ASSEMBLY, which patent application is also assigned to the assignee of the present patent application, and which patent application is also hereby incorporated herein by reference.

Before using the suture anchor and inserter to attach suture to a bone, the suture must be threaded through the transverse bore of the suture anchor and through the lengthwise bore of the inserter. Typically, the suture anchor's transverse bore is relatively short and the inserter's lengthwise bore is relatively long, thereby requiring different threader configurations. By way of example, an ordinary needle threader may be used to thread the suture through the suture anchor's transverse bore, whereas a crochet-hook type of threader may be used to thread the suture through the inserter's lengthwise bore.

In situations where the suture is to be threaded through the suture anchor and the inserter during initial manufacture, it may not be inconvenient for the manufacturer to use different threaders for threading the suture through the suture anchor and the inserter. However, where the suture is to be threaded through the suture anchor and inserter at the time of use, i.e., in the operating room, it can be undesirable for the operating room personnel to use different threaders for threading the suture through the suture anchor and through the inserter. Thus, it is deemed beneficial to have available a single threader which is adapted to thread suture through both (i) relatively short bores, such as those found in a suture anchor, and (ii) relatively long bores, such as those found in an inserter.

OBJECTS OF THE INVENTION

Accordingly, one object of the present invention is to provide a suture threader assembly adapted to thread suture through both suture anchors and inserters.

A further object of the present invention is to provide a suture anchor assembly including a suture anchor, an inserter, a suture, and a suture threader assembly for threading the suture through both the suture anchor and the inserter.

A still further object of the present invention is to provide a method for threading suture through a suture anchor and an inserter.

SUMMARY OF THE INVENTION

These and other objects of the present invention are addressed by the provision and use of a novel suture threader assembly comprising a body having first and second ends, a first suture threader extending from the first end of the body, and a second suture threader extending from the second end of the body.

The objects of the present invention are further addressed by the provision and use of a novel suture anchor assembly comprising a suture anchor having a transverse first bore extending through a proximal end thereof, and an inserter having an axial second bore extending therethrough, and a seat disposed in the second bore for receiving the suture anchor. The suture anchor assembly further includes a suture for threading through the first bore and for threading through the second bore and out a proximal end of the inserter, and a suture threader assembly for threading the suture through the first bore so as to connect the suture to the suture anchor and for thereafter threading the suture through the second bore such that the suture can be used to pull the anchor onto its seat in the second bore.

The objects of the present invention are still further addressed by the provision and use of a novel method for threading suture through a first bore extending transversely through a suture anchor and for threading the suture through a second bore extending lengthwise through an inserter. The method includes the steps of providing a suture threader assembly comprising a body having first and second ends, a first suture threader extending from the first end of the body, and a second suture threader extending from the second end of the body. The suture threader assembly is used by manipulating the body so as to pass the first suture threader through the first bore, positioning the suture in the first suture threader, manipulating the body so as to return the first suture threader through the first bore, whereby to pass the suture through the first bore so as to facilitate attachment of the suture to the anchor, and then removing the first suture threader from the suture. The suture threader is further used by manipulating the body so as to pass the second suture threader into a proximal end of the second bore, through the second bore, and out a distal end of the second bore, positioning the suture in the second suture threader, and manipulating the body so as to return the second suture threader through the second bore, whereby to pass the suture through the second bore and out the proximal end of the second bore.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 4 is a side elevational view of a suture anchor of the sort which the suture threader assembly of FIGS. 1–3 might be used with;

FIG. 6 is a side view of an inserter of the sort which the suture threader assembly of FIGS. 1–3 might be used with;

FIG. 7 is an end view of the proximal end of the same inserter;

FIGS. 8–14 are diagrammatic illustrations showing the suture threader assembly's first suture threader threading suture through the suture anchor;

FIGS. 15–19 are diagrammatic illustrations showing the suture threader assembly's second suture threader threading suture through the inserter.

DETAILED DESCRIPTION OF THE PREFERRED EMBODIMENTS

Figure 1:
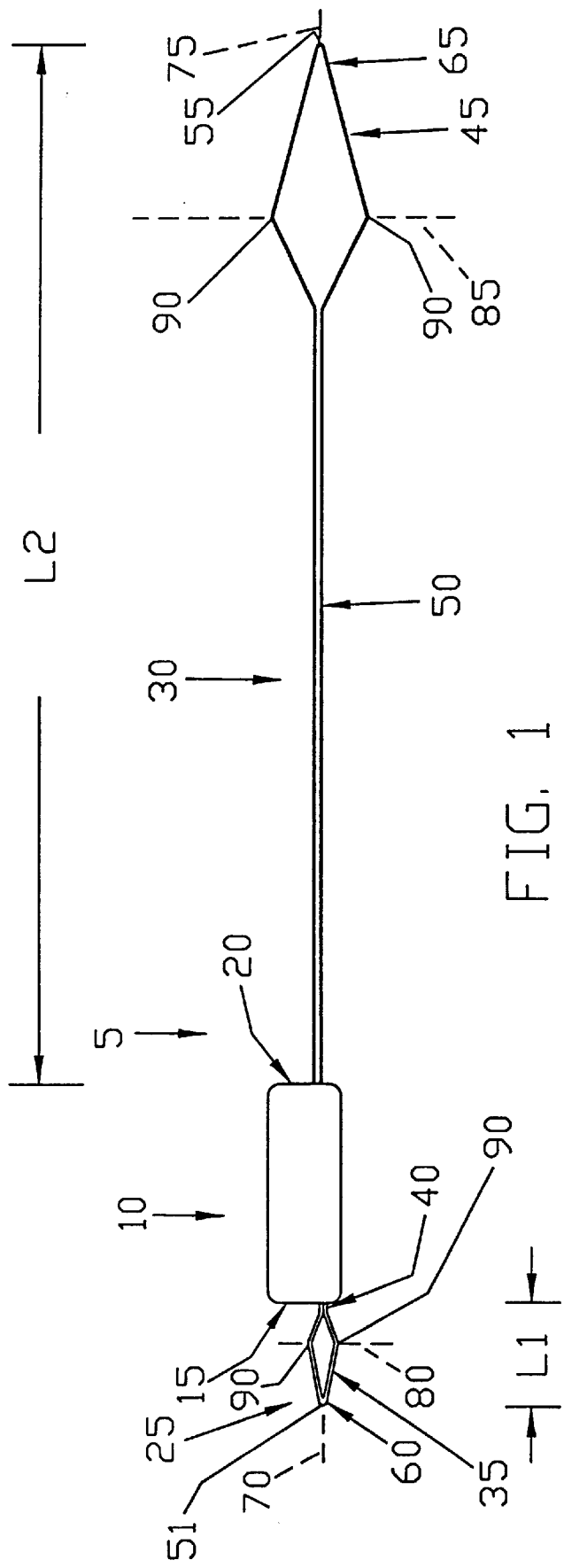
FIG. 1 is a side view of a suture threader assembly formed in accordance with the present invention.

Referring to the drawings, it will be seen that an illustrative embodiment of the present invention includes a suture threader assembly 5 (FIG. 1), a suture anchor 100 (FIGS. 4 and 5), an inserter 200 (FIGS. 6 and 7), and a suture 300 (FIGS. 11–14 and 17–20).

Figure 3:
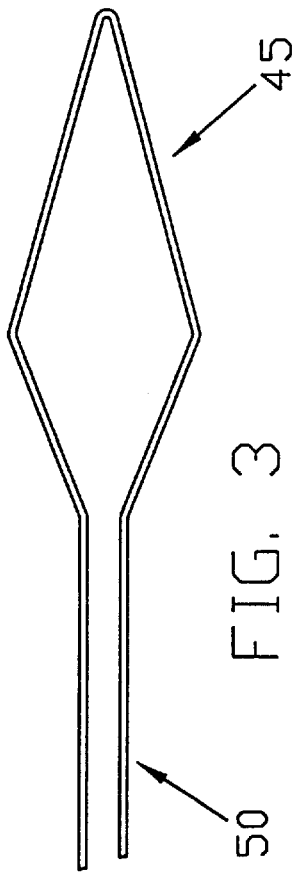
FIG. 3 is an enlarged side view showing the other end of the suture threader assembly shown in FIG. 1.
Figure 2:
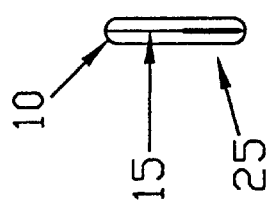
FIG. 2 is an end view of one end of the suture threader assembly shown in FIG. 1.

Looking next at FIGS. 1–3, suture threader assembly 5 includes a body 10 having first and second ends 15 and 20, respectively. A first suture threader 25 extends from first end 15 and a second suture threader 30 extends from second end 20.

First suture threader 25 comprises a substantially closed first loop 35 of a first wire-like material, and a first neck portion 40 of the same first wire-like material. Neck portion 40 interconnects first loop 35 of first suture threader 25 with first end 15 of body 10.

Second suture threader 30 comprises a substantially closed second loop 45 of a second wire-like material, and a second neck portion 50 of the same second wire-like material. Neck portion 50 interconnects second loop 45 of second suture threader 30 with second end 20 of body 10. Second neck portion 50 is significantly longer than first neck portion 40. By way of example but not limitation, second neck portion 50 might be on the order of 10 times the length of first neck portion 40.

Each of the first and second loops 35, 45 substantially comprises a quadrilateral having a point 51, 55 at an end 60, 65 most removed from the body's ends 15, 20. Each of the first and second loops 35, 45 defines (i) a longitudinal axis 70, 75, and a (ii) transverse axis 80, 85 extending perpendicular to the respective longitudinal axes 70, 75.

First suture threader 25 is provided with a length L1 (as measured between its end 60 and the body's first end 15) which is substantially shorter than the second suture threader's length L2 (as measured between its end 65 and the body's second end 20). Transverse axis 80 of first loop 35 is disposed closer to the body's first end 15 than to the first loop's end 60. On the other hand, transverse axis 85 of second loop 45 is disposed closer to its end 65 than to the body's second end 20. Each of the first and second loops 35, 45 is provided with side points 90 which are disposed substantially along the transverse axes 80, 85. The side points 90 of first loop 35 are thus closer to body 10 than to end 60, and side points 90 of second loop 45 are closer to end 65 than to body 10.

The first and second materials of first and second suture threaders 25, 30 may be metal wire, such as stainless steel, or a plastic material wire, preferably round in cross-sectional configuration. The diameter of the wire-like material of first suture threader 25 is substantially less than the diameter of the wirelike material of the second suture threader 30, as will be discussed further hereinbelow.

Figure 5:
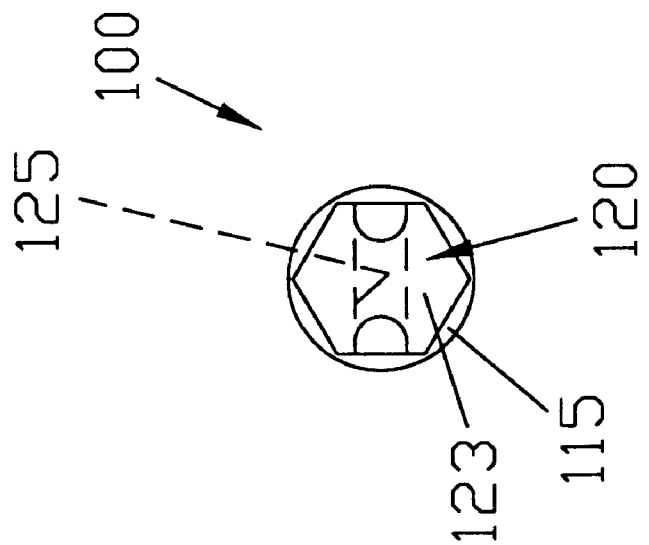
FIG. 5 is a proximal end view of the suture anchor of FIG. 4.
Figure 4:
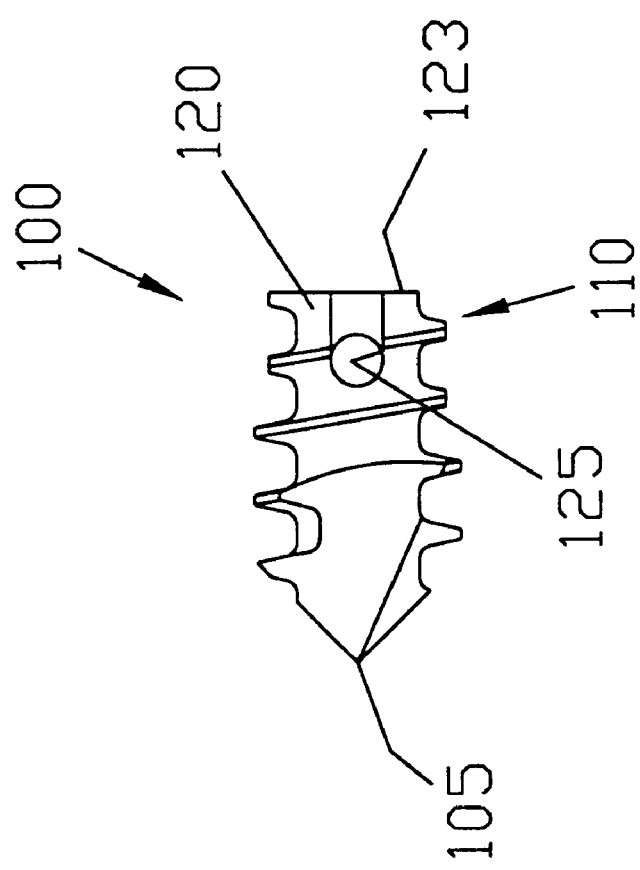

In FIGS. 4 and 5, there is shown a suture anchor 100, which is typically made of metal. Suture anchor 100 is of a generally cylindrical configuration and is provided with a distal end 105, which is pointed or otherwise configured so as to penetrate bone. At a proximal end 110 thereof, suture anchor 100 is reduced in diameter so as to provide a proximally-facing annular flange 115 and a proximally-extending dowel 120. Preferably dowel 120 has a non-circular (e.g., hexagonal) cross-section, whereby anchor 100 may be rotated by a deployment tool (e.g., inserter 200). Dowel 120 terminates in a proximal end surface 123. The dowel 120 defines a transverse bore 125 extending therethrough, side to side. Bore 125 is adapted to receive suture 300, as will be further described hereinbelow. Preferably suture anchor 100 is similar to the sort of anchor disclosed in the aforementioned U.S. patent application Ser. No. 08/514,613.

Referring next to FIGS. 6 and 7, it will be se en that inserter 200 is provided with a longitudinal bore 205 extending lengthwise therethrough and stepped with a front broach 207 so as to provide a distally-facing annular flange 210 defining a suture anchor seat for receiving suture anchor 100. Preferably broach 207 has a non-circular (e.g., hexagonal) cross-section corresponding to the cross-sectional shape of the anchor's dowel 120, whereby inserter 200 can be used to rotate anchor 100 so as to deploy the anchor in bone, in the manner well known in the art. Inserter 200 terminates in a distal end surface 212. Preferably longitudinal bore 205 includes a countersink 215 near the proximal end of inserter 200, so as to facilitate entry of the second suture threader 30 into the inserter, as will hereinafter be discussed. Thus it will be seen that inserter 200 generally comprises an elongated bore passing from one end of the inserter to the other, with the distal end of that elongated bore being configured to receive the suture anchor, and the proximal end of that elongated bore being configured to facilitate entry of second suture threader 30 into that elongated bore.

It is to be appreciated that the inserter's longitudinal bore 205 is generally significantly longer than the suture anchor's transverse bore 125; and the inserter's longitudinal bore 205 is generally also significantly wider than the suture anchor's transverse bore 125.

Figure 8:
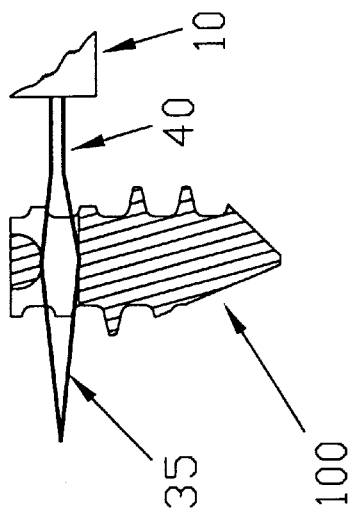
Figure 9:
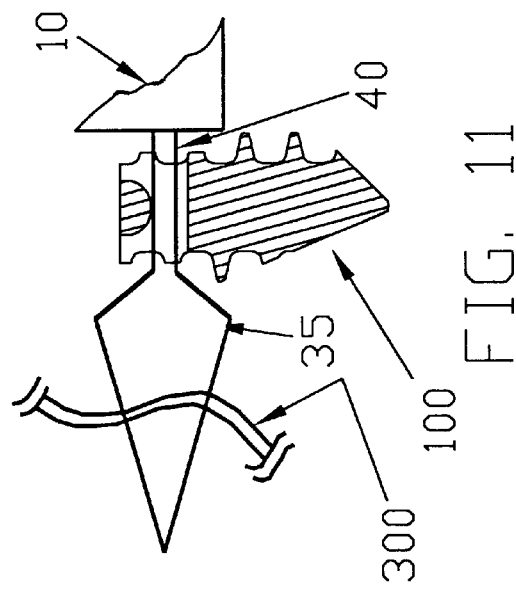
Figure 10:
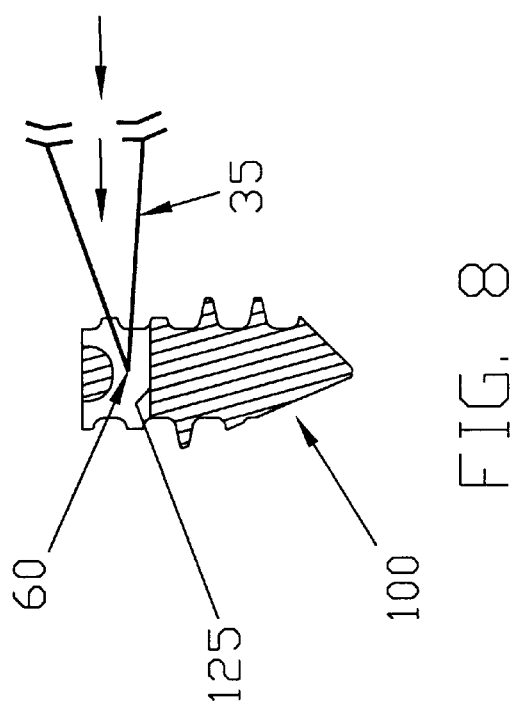

In operation, the suture threader assembly 5 is typically used first to attach suture 300 to suture anchor 100 (FIGS. 8–14). More particularly, an operator grasps suture threader assembly body 10 and directs first suture threader end 60 into suture anchor bore 125 (FIG. 8). As first loop 35 is urged into bore 125, the loop 35 compresses (FIG. 9), permitting loop 35 to travel through bore 125. As noted above, the first loop 35 is made of metal, such as stainless steel, or a plastic material, which permits the first loop to compress into bore 125. A first loop material found suitable is round 304 stainless steel wire, ½ hard, of a diameter of about 0.003 inch.

Figure 11:
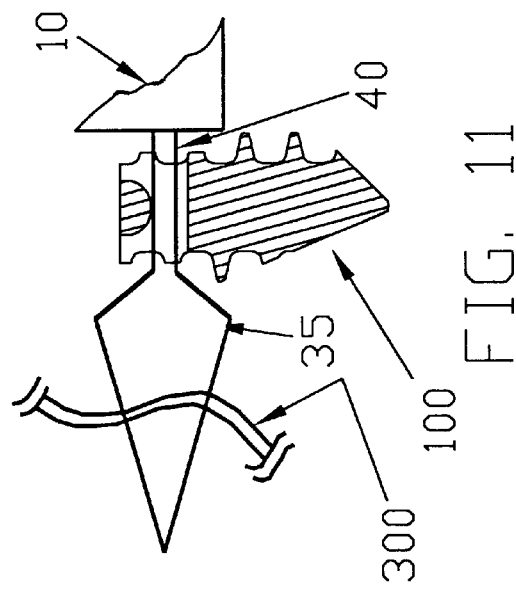
Figure 18:
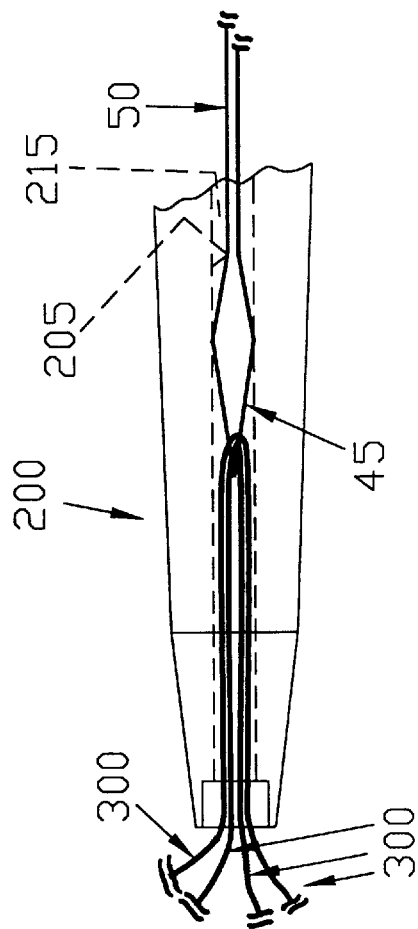

Upon emerging from bore 125, first loop 35 may naturally regain sufficient of its loop configuration (FIG. 10) to permit threading suture 300 therethrough (FIG. 11). If not, the operator may easily pry open first loop 35. Once suture 300 is in first loop 35, loop 35 is drawn back by manipulation of body 10 through bore 125 (FIG. 12) so as to thread the suture through the suture anchor's bore 125 (FIG. 13). One end of the suture may then be pulled through the bore 125 to slidably secure the suture 300 to anchor 100 (FIG. 14).

Figure 19:
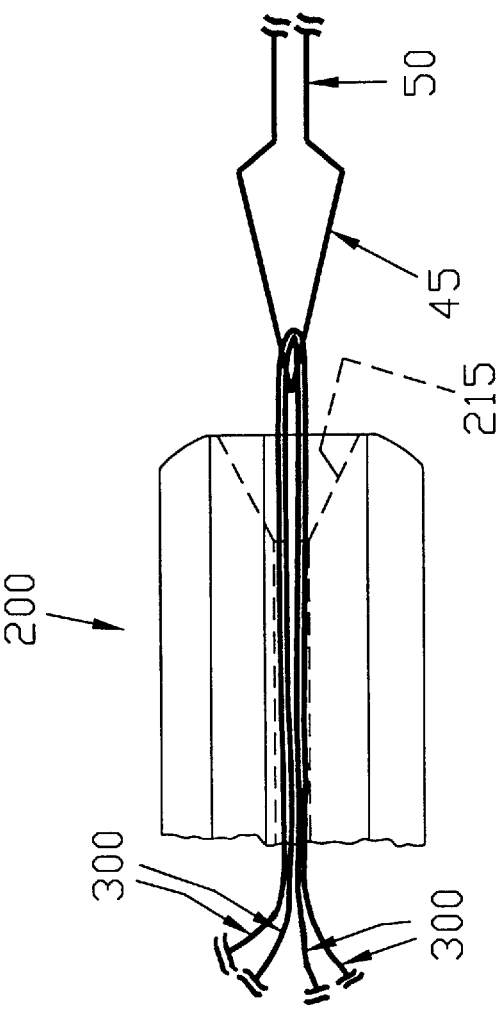
Figure 20:
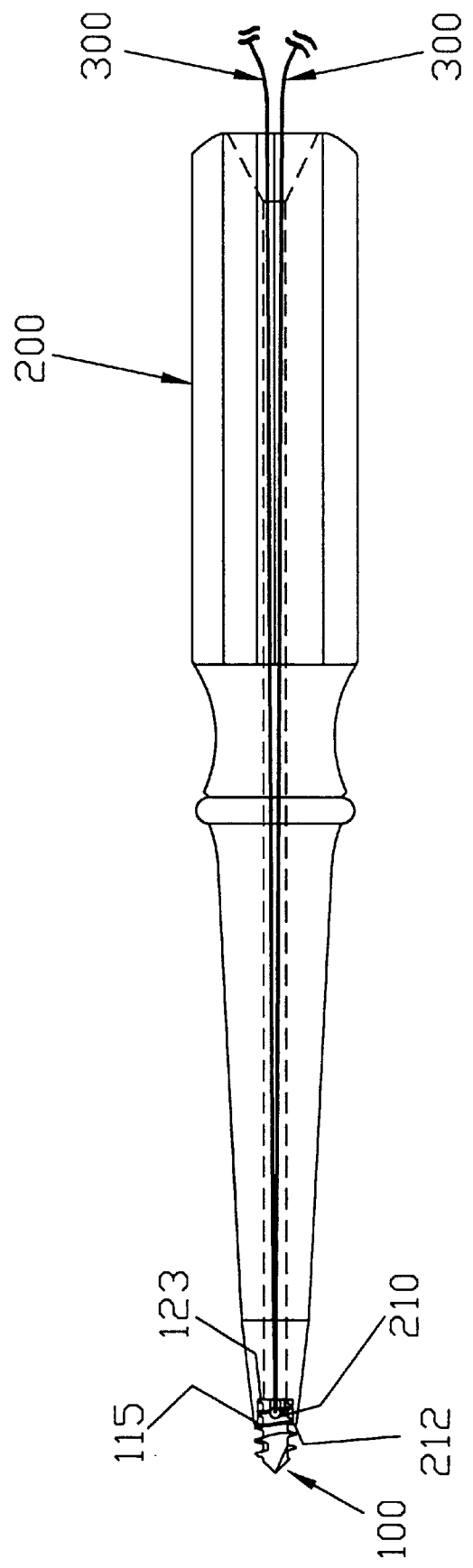
FIG. 20 is a schematic illustration showing a suture anchor, inserter and suture, wherein the suture has been appropriately threaded through the suture anchor and inserter, and the suture anchor is mounted in the inserter.

Having slidably secured suture 300 to suture anchor 100, it is desirable to then thread suture 300 through inserter 200. However, due to the elongated configuration of inserter 200, first suture threader 25 is inadequate for this purpose and second suture threader 30 must be used. More particularly, the operator, by grasping body 10, directs second loop point 55 into inserter 200 at the proximal countersink 215 (FIG. 15) and then down the length of bore 205. Because of the wire-like structure of second loop 45, loop 45 readily compresses to enter and pass through the inserter countersink 215 and then bore 205 (FIG. 16). Like the first suture threader 25 discussed above, the second suture threader 30 may be made of a metal or plastic wire-like material, preferably round 304 stainless steel wire, ½ hard, of about 0.012 inch diameter. The second loop 45 is of a material and of a dimension suitable for permitting collapse of loop 45 upon entering and passing through countersink 215 and bore 205 and for self-expansion of loop 45 upon emerging from bore 205 and broach 207 (FIG. 17). Again, if loop 45 does not naturally re-expand to a size sufficient to easily receive a suture, another tool (not shown) can be used to pry the loop open. Both free ends of suture 300 are then threaded through second loop 45 (FIG. 17). Next, the loop is drawn back through broach 207, bore 205 (FIG. 18), and out the proximal countersink 215 (FIG. 19). The suture threader assembly 5 is then disengaged from suture 300.

By grasping the two free ends of suture 300, the operator may then draw suture anchor 100 into distal broach 207 until the anchor's annular flange 115 engages the inserter's distal end surface 212 and the anchor's proximal end surface 123 engages the inserter's annular flange 210 (FIG. 20) so as to seat anchor 100 in inserter 200. Suture anchor 100 and inserter 200 may then be used in ways well known in the art to attach suture 300 to a bone.

After suture 300 has been threaded through suture anchor 100 and inserter 200, the suture threader assembly 5 may be disposed of. Inasmuch as body 10 is typically made of a rigid plastic material and the remainder of the suture threader assembly 5 is made of a metal or plastic wire, the assembly is inexpensive to make and readily disposable without undue cost.

It is, of course, possible to use the suture threader assembly 5 in conjunction with suture anchors and inserters other than those shown in FIGS. 4–20. By way of example, suture threader assembly 5 might be used with a suture anchor and inserter such as shown in the aforementioned U.S. Pat. No. 5,411,506, or the suture threader might be used with other suture anchors and/or inserters. Among other things, it should be noted that suture threader assembly 5 might be used with suture anchors comprising means other than screw threads for retaining the suture anchor in bone, e.g., the assembly might be used with suture anchors comprising barbs or expandable bodies. Suture threader assembly 5 might also be used with suture anchors having a suture-receiving bore extending in a direction other than transverse, e.g., the suture threader assembly 5 might be used with a suture anchor having a suture-receiving bore extending in a longitudinal direction along the length of the anchor. In short, suture threader assembly 5 might be used with any suture anchor system of the sort comprising a suture anchor having a relatively short bore and an inserter having a relatively long bore.

There is thus provided a suture threader which serves the dual purposes of threading suture through both suture anchors and inserters. There is further provided a suture assembly including a suture anchor, a suture, an inserter, and a suture threader for threading the anchor and the inserter. There is still further provided a method for fixing suture to a suture anchor and passing the suture through an inserter, using one tool for both tasks.

It is to be understood that the present invention is by no means limited to the particular construction and method steps herein disclosed and/or shown in the drawings, but also comprises any modifications or equivalents within the scope of the claims.

What is claimed is:

1. A suture anchor assembly comprising:
   a suture anchor having a transverse first bore therethrough proximate a proximal end thereof;
   a suture anchor inserter having an axial second bore therethrough and a suture anchor seat disposed in said second bore for receiving and retaining said suture anchor;
   a suture for disposition in said first bore and for extending through said second bore and out a proximal end of said inserter; and
   a suture threader assembly for threading said suture through said first bore to connect said suture to said anchor and for thereafter threading said suture through said second bore such that said suture is operable to pull said anchor into said second bore and onto said anchor seat.

2. A suture anchor assembly according to claim 1 wherein said anchor is provided with distal and proximal ends, said anchor distal end being configured to penetrate bone, said anchor being generally cylindrically-shaped, and said proximate end being of reduced diameter so as to provide a proximal-facing annular flange on said anchor.

3. A suture anchor assembly according to claim 2 wherein said suture anchor seat of said inserter comprises a distally-facing annular flange engageable by said suture anchor annular flange to seat said suture anchor in said inserter second bore.

4. A suture anchor assembly according to claim 1 wherein said first bore extends from side-to-side of said suture anchor reduced diameter portion.

5. A suture anchor assembly according to claim 1 wherein said suture threader assembly comprises a body having first and second ends, a first suture threader extending from said body first end, and a second suture threader extending from said body second end, said first suture threader being adapted for said threading of said suture through said first bore, and said second suture threader being adapted for said threading of said suture through said second bore.

6. A suture anchor assembly according to claim 5 wherein said first suture threader comprises a substantially closed first loop of first wire-like material and said second suture threader comprises a substantially closed second loop of second wire-like material.

7. A suture anchor assembly according to claim 6 wherein each of said loops substantially comprises a quadrilateral having a point at an end most removed from said body.

8. A suture anchor assembly according to claim 7 wherein each of said loops has opposed side points, said side points in said first loop being closer to said body than to said First loop end, and said side points of said second loop being closer to said second loop end than to said body.

9. A method for fixing suture to a suture anchor of the sort having a first transverse bore therethrough and for passing said suture through a second bore extending lengthwise through a suture anchor inserter, said method comprising the steps of:

provinding a suture threader assembly comprising a body having first and second ends, a first suture threader extending from said body first end, and a second suture threader extending from said body second end;

manipulating said body to pass said first suture threader in a first direction through said first bore;

positioning a portion of said suture in said first suture threader;

manipulating said body to pass said first suture threader in a second direction through said first bore so as to pass said suture through said bore to facilitate attachment of said suture to said anchor;

removing said suture from said first suture threader;

manipulating said body to pass said second suture threader into a proximal end of said second bore, through said second bore, and out a distal end of said second bore;

positioning a portion of said suture in said second suture threader; and manipulating said body so as to return said second suture threader through said second bore distal end and through said second bore so as to pass said suture through said second bore and out said proximal end of said second bore.

10. A method according to claim 9 wherein said first suture threader comprises a first loop having a first point remote from said body and said second suture threader comprises a second loop having a second point remote from said body;

said passing of said first suture threader in said first direction through said first bore comprises urging said first point through said first bore to compress said first loop which, upon emerging from said first bore, is expandable to again form a loop configuration;

said positioning of said suture in said first suture threader comprises passing said suture into said first loop;

passing said suture through said first bore comprises pulling said first suture threader, with said suture therein, back through said first bore for said attachment of said suture to said suture anchor;

said passing of said second suture threader distally through said second bore comprises inserting said second loop end into said proximal end of said second bore and urging said second point through said second bore to compress said second loop which, upon emerging from said second bore at said distal end thereof, expands to form a loop configuration;

said positioning said suture in said second suture threader comprises passing said suture into said second loop; and said returning of said second suture threader through said second bore in a proximal direction comprises pulling said second suture threader, with said suture therein, back through said second bore for stringing said suture through said second bore and out said proximal end of said second bore.

* * * * *